United States Patent [19]

Nelson et al.

[11] Patent Number: 4,531,401
[45] Date of Patent: Jul. 30, 1985

[54] IMPACT TEST APPARATUS

[75] Inventors: Jordan R. Nelson, Pennington; Remo A. Funari, Trenton, both of N.J.

[73] Assignee: RCA Corporation, Princeton, N.J.

[21] Appl. No.: 564,914

[22] Filed: Dec. 23, 1983

[51] Int. Cl.³ .............................................. G01N 3/30
[52] U.S. Cl. ..................................................... 73/12
[58] Field of Search ................................. 73/12, 79, 87

[56] References Cited

U.S. PATENT DOCUMENTS

| | | | |
|---|---|---|---|
| 1,809,347 | 6/1931 | Martin | 73/12 |
| 3,224,249 | 12/1965 | Ford et al. | 73/12 |
| 3,426,578 | 2/1969 | Bergs et al. | 73/12 |

OTHER PUBLICATIONS

D. C. Guidici-"Fracture Strength of Silicon Wafers'-'-Electronic Packaging & Production, vol. 18, No. 4, Apr. 1978, pp. 98-100.

Ed Galli, "Properties Testing: Impact" Plastics Compounding, Sep./Oct. 1982, pp. 18-20, 22, 24, 26-28.

*Primary Examiner*—Charles A. Ruehl
*Attorney, Agent, or Firm*—Birgit E. Morris; Edward J. Sites

[57] ABSTRACT

An apparatus for guided free fall impact testing of aerodynamically unstable disc shaped articles such as molded records. The apparatus has a vertical guide means which has guide rails and guide slides for correcting attitude deviations from the vertical of a disc shaped article as it free falls through the guide means. The apparatus also includes means for releaseably securing a disc shaped article at a preselected height. The apparatus also includes a contact plate for terminating the free fall of the disc shaped article and imparting the resulting impact force at a point on the outer diameter of the article.

6 Claims, 4 Drawing Figures

U.S. Patent  Jul. 30, 1985  4,531,401
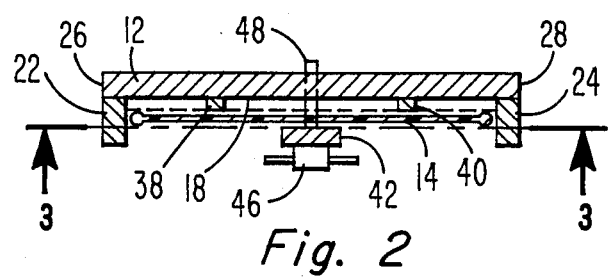
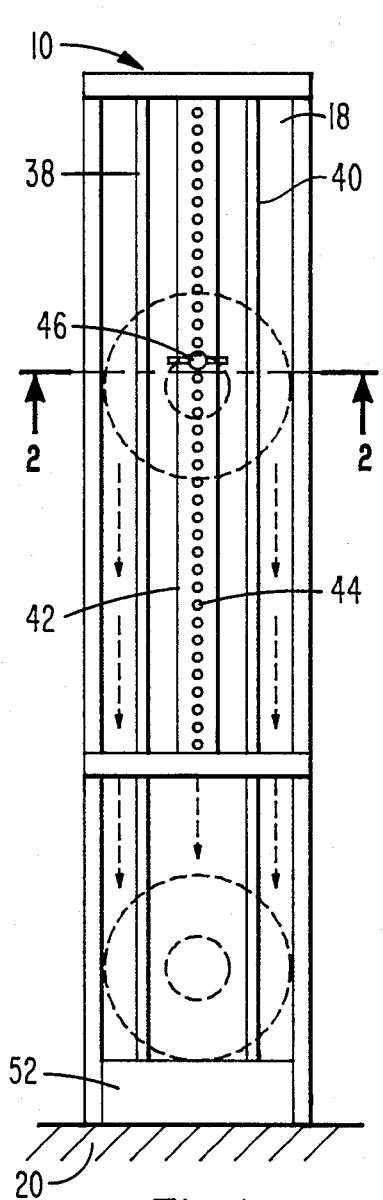
Fig. 1
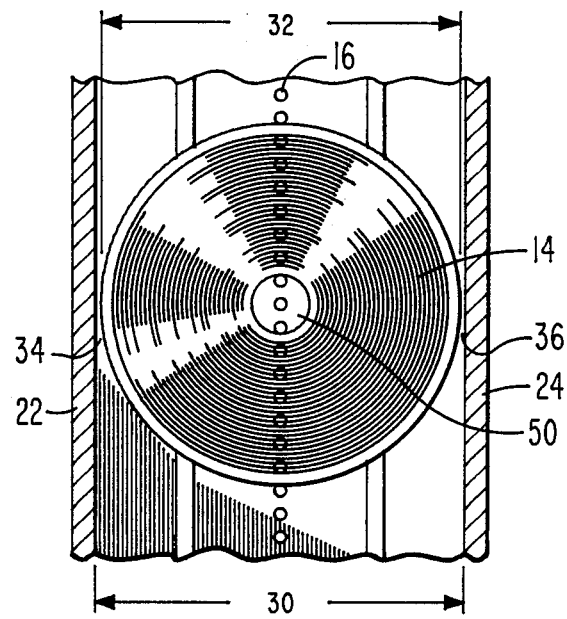
Fig. 3
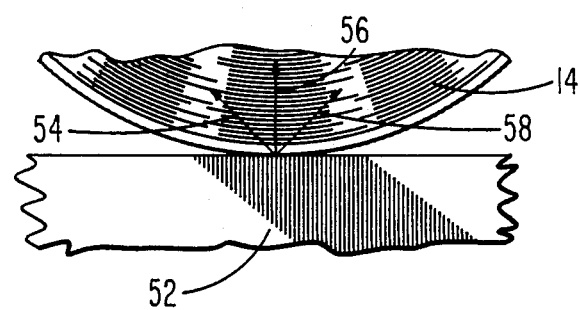
Fig. 4

IMPACT TEST APPARATUS

This invention relates to a test apparatus for use in measurement of impact strength at a point on the outer diameter edge of an aerodynamically unstable disc shaped article and more particularly is concerned with drop testing of molded plastic records to determine the impact strength properties of the records.

BACKGROUND OF THE INVENTION

Impact strength is a measurement of the ability of a material to resist high rate loading of force. The evaluation of impact strength is used for a number of purposes. Impact strength is used to preliminarily screen materials to determine if the materials have sufficient resistance to breakage when impacted with a force of the magnitude expected to be encountered in normal use of a product made from the material as well as under anticipated abnormal conditions such as when the product is accidently dropped.

Impact strength testing is also used for quality control evaluations to determine the variations, if any, from batch to batch of material and more importantly, to determine if a given batch of material has the specified properties required to make the end product. Impact strength monitoring is particularly important in the manufacture of plastic products. The plastic compositions used to mold the products are generally made of a number of distinctly different components some of which are highly subject to variations in properties as a result of minor changes in formulations and processing conditions. An example of the type of plastic compositions which must be closely monitored for impact strength are those used for pressing records, especially capacitive electronic discs. Record molding compositions typically include a theomoplastic resin such as a polyvinylchloride resin which itself can vary widely from batch to batch, fillers such as carbon black, and various additives such as lubricants, processing additives, antistatic agents and the like. The addition of fillers, and in particular, carbon black, to record molding compositions is known to have a significant detrimental effect on the impact strength of record molding compositions. The addition of relatively large amounts of carbon black is, however, essential in the manufacture of certain types of records, such as capacitive electronic discs, in order to obtain the electrical conductance required for capacitance electronic playback. Because of the close and adverse relationship between impact strength and carbon black loading quality control testing of impact strength is exceptionally important in the record pressing art. Impact strength testing is, of course, also an important quality control tool in the manufacture of other products in addition to records.

Impact strength testing is also widely used in experimental development of new compositions. The effect of changes in the chemical composition, processing conditions and other similar variables can be relatively simply determined by measuring the affect on impact strength.

Various methods had been suggested to measure impact strength. One of the most widely used tests is the Izod impact test which is described in ASTM Standard D-256. In the Izod impact test, a sample of a specified standard size and shape is prepared with a notch cut into the sample at a predetermined position. The sample is clamped in a stationary position and a weighted pendulum is released from a known height so as to contact the test sample with a known force to determine the impact strength of the material under evaluation.

Another commonly used test, generally referred to as the dropped weight test or the Gardner test, is described in ASTM D 3059. In this test, a test piece of a known weight is dropped from a known height onto a stationary test specimen of the material under evaluation. The calculated force developed by the test piece required to break the test specimen is the impact strength.

Tests of the above type have not been found to be fully correlatable with the impact strength properties of products made from the tested material. The variations in impact strength properties which are obtained on the test sample and the actual product are believed to be due in part to the differences in the stresses formed during molding of the product and also the conditions under which impact forces are typically applied to the actual product as compared to the standard size test sample. In the conventional tests, such as the Izod test or the Gardner test, the material to be evaluated is held in a stationary position and is struck with an accelerating, moving object, i.e., the pendulum or the falling test piece. However, under conditions normally encountered actual use of many products, it is the product which is normally the accelerating, moving element which makes contact with a stationary body. This occurs, for example, when a molded record is dropped wherein the record is the moving element and the floor, or the like, is the stationary body which is contacted by the record. A further possible cause of the differences in impact strength values obtained under the standarized test conditions and in actual use can be attributed to the difference in the shape of standard test pieces and that of the actual end product. The test samples are made in a specified shape, such as a rectangular bar for testing. The end product, however, usually has a substantially different shape from the standard test piece and these differences can substantially effect the results obtained on impact.

Suggestions have been made of test methods to determine impact strength properties which are more relevant to conditions of actual use by employing test methods designed to simulate the actual drop conditions encountered by the final product. This type of testing is, however, limited to objects which have a weight or a shape or a combination of both such that the force of gravity will result in a predictable, repeatable free fall path. A type of test apparatus which can be used for evaluating products such as loaded cartons is disclosed by Ford et al in U.S. Pat. No. 3,224,249 entitled "Adjustable Fixture For Drop Testing." Aerodynamically shaped articles can also be tested by free fall drop of the final product. Such a type or apparatus is disclosed in Bergs et al in U.S. Pat. No. 3,426,578 entitled "Impact Test Apparatus" discloses a test apparatus in which a specimen, such as an artillery shell having an aerodynamically stable shape, is evaluated to determine its impact resistance.

Free fall impact testing apparatus of the type heretofore suggested in the prior art cannot be utilized, however, to satisfactorily evaluate the impact strength properties of lightweight products which are inherently aerodynamically unstable. Lightweight aerodynamically unstable articles when dropped will tend to tumble during free fall and cause uncontrollable variations in the forces developed during the free fall and also uncontrolled variations in the point of impact from test to test. The results obtained under these test conditions are so erratic that the test results are of little in any value. In this regard, it has been found to be especially difficult to evaluate thin disc shaped articles having a diameter which is substantially greater than the thickness of the article, for example, a disc having a diameter of about 50 or more times than its thickness. A specific product of this type which has heretofore been essentially impossible to evaluate with any degree of reliability by free fall drop testing has been molded plastic records. A typical long playing record has an outer diameter of about 12 inches (30.48 cm), a thickness of about 1/16th of an inch (0.16 cm) and is made of a relatively lightweight filled plastic composition. The unfavorable ratio of the outer diameter to the thickness of a molded record tends to cause tumbling in drop testing the effect of which is further complicated by the presence of the center hole which is conventionally formed in records as the center hole appears to further increase the instability of records during free fall.

Ideally to evaluate the impact strength of a molded record the record should be allowed to vertically free fall so as to be impacted vertically at a point on its outer diameter edge. This type of impact would impart the greatest concentration of impact force through the body of the record which could be expected to be encountered in actual use, and thus, represents the best test condition for evaluating free fall breakage characteristics of the record. As indicated above, if a conventional record is allowed to free fall, it will tumble in an uncontrolled manner and almost never will land squarely on the outer diameter edge and the results obtained are erratic and unreliable with regard to the impact strength characteristics of the molded record.

What would be highly advantageous would be an apparatus for evaluating impact strength in which an aerodynamically unstable article, such as a disc or the like, could be subjected to controlled vertical free fall so as to impact consistently on the outer diameter edge thereof so as to obtain repeatable, reliable results with regard to impact strength.

BRIEF SUMMARY OF THE INVENTION

An apparatus is provided for guided free fall impact testing of aerodynamically unstable disc shaped articles such as molded records. The apparatus has a vertical guide means which has guide rails and guide slides for correcting attitude deviations from the vertical of a disc shaped article as it free falls through the guide means: the apparatus also includes a releaseable pin for securing a disc shaped article at a predetermined height and a contact plate for terminating the free fall of the disc shaped article.

BRIEF DESCRIPTION OF THE DRAWING

FIG. 1 is a front illustration of the impact test apparatus of this invention.

FIG. 2 is an illustration in partial cross-section of the apparatus of FIG. 1 taken as indicated by the line and arrows 2, 2 on FIG. 1.

FIG. 3 is an illustration taken as indicated by the lines and arrows 3, 3 of a portion of the apparatus of FIG. 1.

FIG. 4 is an illustration of a portion of a record at a point of impact after guided free fall.

DETAILED DESCRIPTION OF THE INVENTION

In describing the apparatus 10 of this invention and the operation thereof, the term "guided free fall" will be utilized. The term guided free fall is to be understood to mean in the context of this invention, the effect obtained when an object, typically an aerodynamically unstable article such as a disc, is allowed to fall vertically between spaced apart guide rails and guide slides which correct any deviation in the attitude of the falling article from a vertical drop path.

The apparatus 10 of this invention is comprised of the back support portion 12 which is air impervious to prevent air drafts from disturbing the free fall of articles 14 to be evaluated in the apparatus 10 of this invention. The back support portion 12 as illustrated includes a vertical line of spaced apart apertures 16 defined therein, the function and purpose of which will be explained in greater detail hereinafter.

The back support portion 12 of the apparatus 10 of this invention has a flat inner surface 18, which in use is positioned perpendicular to the ground 20.

The back support portion 12 further has mounted on the flat inner surface 18 first and second guide rails 22, 24. As illustrated in FIGS. 1 and 2, the first and second guide rails 22, 24 are positioned at the outer edges 26, 28 of the back support portion 12. The first and second guide rails 22, 24 are parallel to each other and are positioned vertical with this respect to the ground 20. The first guide rail 22 and the second guide rail 24 are spaced apart from each other at a predetermined distance, which distance 30 is slightly greater than the diameter 32 of the article 14 which is to be evaluated. The guide rails 22, 24 also extend a sufficient outward distance from the back support 12 so as to control the lateral path of free fall of the article 14 to be evaluated, such as a record illustrated in the figures. The predetermined distance 30 is critical, being a distance sufficient to provide an adequate space between the outer edges of the article 14 being evaluated so as to prevent drag of the article's edges on the guide rails 22, 24 during free fall. The predetermined distance 30 may likewise also sufficiently narrow so as to cause prompt correction of any lateral shift to the left or right during free fall of the article 14. The predetermined distance 30 has been found to advantageously ⅛ to ¼ of an inch (3.17 to 6.35 mm) wider than the diameter 32 of the article 14 under evaluation.

The back support portion 12 also has mounted on the flat inner surface 18 a pair of rear guide slides 38, 40. As illustrated in the preferred embodiment the guide slides 38, 40 are mounted on the flat inner surface 18 in a parallel spaced apart relationship from each other. The rear guide slides 38, 40 are advantageously positioned about ¼ of the distance 30 from the first guide rail 22 and the second guide rail 24, respectively. As will be more apparent hereinafter, this spacing places the slides 38, 40 at about one half the radial distance to the center of the article 14 to be evaluated, which result in the rearguide slides 38, 40 having maximum area for guiding contact of the article 14 when utilized with the additional guide to be hereafter disclosed.

The rearguide slides 38, 40 have a thickness and a width sufficient to prevent dragging contact of the article 14 with the inner surface 18 of the back support portion 12 during free fall of an article 14 in the apparatus 10 of this invention. It has been found that if the rear guide slides 38, 40 extend from the flat inner surface 18 about ¼ of an inch (6.35 mm) or more and the width of the guides is about ½ to ¾ of an inch (12.7 to 19 mm), satisfactory results are readily obtained.

A forward center guide slide 42 is positioned vertically in the center of the apparatus 10. The forward guide slide 42 is spaced apart from the rear guide slides 38, 40 so as to form a guide channel as defined by the dashed lines on FIG. 2. The rearward guide slides 38, 40 and the forward guide slide 42 limit the forward and reverse changes in attitude of an article 14 during free fall of the article under evaluation. The forward guide slide 42 has defined therein a series of spaced apertures 44 which are aligned with the spaced apertures 16 in the back support portion 12. The apertures 16, 44 are spaced apart by set measured distances from each other so that the height of the distance required to cause breakage on impact of an article 14 under evaluation can be determined by either a calculation of the actual force developed on impact or by reference to a standard corresponding to the measured height of the drop.

A removable pin 46 is provided which has a dowel 48 which can be inserted through an aperature 44 in the forward guide slide 42 and then either through or in contact with the bottom of the article 14 to be evaluated and then through an aperture 16 in the back support portion 12. The pin 46, in combination with the apertures 16, 44, provide a holding means for securing the article 14 to be tested in a stationary position prior to actually being dropped. When the article 14 is a part which has a hole in the center thereof, such as a record, the center hole 50 in the part can be used in combination with the pull pin 46 to result in simpler centering of the article 14 within the apparatus 10 prior to drop testing.

The forward guide slide 42 can be terminated at a point somewhat less than the entire length of the apparatus 10 as shown in FIG. 1 as once the article 14 to be tested has travelled a substantial distance within the apparatus 10, the free fall path can be adequately maintained in a stable aerodynamic configuration by the combination of the rear guide slides 38, 40 and the guide rails 22, 24. Shortening of the forward guide rail is of substantial advantage in that it facilitates the removal of the article 14 or the fractured parts thereof from the apparatus after the article 14 is dropped during a test evaluation.

The apparatus 10 of this invention also includes at the base thereof an impact plate 52 for terminating the guided free fall of the article 14. The impact plate 52 is preferably of a flat configuration so that there is substantial point impact contact at the edge of the article 14. The impact plate 52 is made of a material which is substantially inelastic such as a hardened steel plate so that the edge contact provides transfer of the substantial entire impact force into the article 14.

In use, it is preferable to initially spray the guide rails 22, 24 and the guide slides 38, 40, 42 with a lubricant such as a Teflon spray so as to reduce the friction and drag or the test article 14 as it is dropped through the apparatus 10. After the optional spraying of the lubricant, the article 14 to be evaluated, which as illustrated in figures is a record, is placed in the apparatus 10 between the first and second guide rails 22 and 24, and the rearward guide slides 38, 40 and the forward guide slide 42. The pin 46 is inserted into an appropriate predetermined aperture 44 in the front guide slide 42 and through or under the article 14 then into an aperture 16 in the back support portion 12. The article 14 is then allowed to come to a complete rest. The pin 46 is then removed and the article 14 is allowed to undergo guided free fall through the apparatus 10. If the article 14 during free fall moves to the left to right, the drop path is corrected to the vertical by the first or second guide rails 22, 24 or both as required. If the article 14 during guided free fall starts to tumble, that is, move forward or backwards, the required correction back to the vertical drop path is made by contact with the rearward guide slides 38, 40 and/or the forward guide slide 42. The article 14 is allowed to drop in this fashion until it contacts the impact plate 52 wherein an impact force is imparted to the article 14 as indicated by the arrows 54, 56 and 58 shown in FIG. 4. The height of the drop is adjusted as required either upwardly or downwardly until consistent results are obtained with regard to impact strength as indicated by a uniform pattern of breakage, when released from a given test height.

Using the apparatus 10 of this invention it has been found that the highly repeatable impact breakage data can be obtained with regard to aerodynamically unstable articles such as records and the like. The impact strength information which is obtained used in the apparatus 10 of this invention is directly correlatable to the impact strength performance encountered during actual use of the article 14 and thus are highly reliable for determining suitability of materials and processing conditions for use in the manufacture of a given article 14.

What is claimed:

1. An apparatus for testing the guided free fall impact strength at a point on the outer diameter of an aerodynamically unstable disc shaped article of a predetermined diameter and a predetermined thickness, said apparatus comprising in combination:

a vertical guide means for directing the disc shaped article during testing in vertical guided free fall from a preselected height, said vertical guide means having a vertical substantially air impervious back support portion of at least said preselected height having a flat inner surface, a first guide rail and a second guide rail; said guide rails being positioned vertically on the flat inner surface spaced apart from each other by a given distance which is wider than the predetermined diameter of the article and extending outwardly from the inner surface by a given amount which is greater than the predetermined width of the article with the given distance and the given amount of extension being sufficient to provide lateral guidance during free fall of the article to maintain the fall direction of the article in a substantial vertical direction;

a holding means cooperatively engagable with the guide means for releaseably securing the disc shaped article at the preselected height within the guide means; and impact means positioned at the bottom terminal end of the guide means for terminating the guided free fall of the disc shaped article after the disc shaped article has fallen the preselected height and thereby imparting to a point on the outer diameter of the disc shaped article substantially all of the impact force developed during the guided free fall.

2. The apparatus according to claim 1 wherein the given distance of separation of the guide rails is about ⅛ to ¼ of an inch (3.17 to 6.35 mm) greater than the predetermined diameter of the disc shaped article.

3. The apparatus according to claim 1 wherein the guide means further includes a first rear guide slide, a second rear guide slide and a center forward guide slide; said first and second rear guide slides being positioned on the inner surface of the rear support portion in a vertical spaced apart relationship to each other with said center forward guide being spaced forward from the rear guide slides by a distance greater than the predetermined thickness of the article and being centrally located between the first and second rear guide slides so that the combination of the rear guide slides and the forward guide slide provide correction of rearward and forward changes in the attitude of the article during free fall so as to maintain the article in a substantially vertical free fall path.

4. The apparatus according to claim 3 wherein the first rear guide slide is positioned on the inner surface parallel to the first guide rail and spaced apart therefrom by a distance equivalent to about one half of the radial width of the article and said second rear guide slide is positioned on the inner surface parallel to the second guide rail and spaced apart therefrom by a distance equivalent to about one half of the radial width of said article.

5. The apparatus according to claim 1 wherein the guide means includes a series of vertically spaced apertures in the center thereof and said holding means is comprised of a pin adapted to extend through said apertures and be engaged thereby so as to hold an article to be evaluated at the preselected height within said guide means and wherein when the pin is removed the article is allowed to fall through the guide means.

6. The apparatus according to claim 5 wherein the apertures are defined in the back support portion and in the center forward guide slide with the apertures in the back support portion being axially aligned with the apertures in the center forward guide slide.

* * * * *